US008569371B2

(12) United States Patent  
Ratkaj et al.

(10) Patent No.: US 8,569,371 B2  
(45) Date of Patent: Oct. 29, 2013

(54) CRYSTAL FORMS OF O-DESMETHYLVENLAFAXINE FUMARATE

(75) Inventors: Marina Ratkaj, Zagreb (HR); Gustavo Frenkel, Beer Sheva (IL)

(73) Assignee: Pliva Hrvatska D.O.O., Zagreb (HR)

( * ) Notice: Subject to any disclaimer, the term of this patent is extended or adjusted under 35 U.S.C. 154(b) by 252 days.

(21) Appl. No.: 13/074,364

(22) Filed: Mar. 29, 2011

(65) Prior Publication Data

US 2011/0237680 A1  Sep. 29, 2011

Related U.S. Application Data

(60) Provisional application No. 61/318,638, filed on Mar. 29, 2010, provisional application No. 61/327,239, filed on Apr. 23, 2010.

(51) Int. Cl.
  *A01N 37/00* (2006.01)
  *A61K 31/19* (2006.01)
  *A01N 47/06* (2006.01)
  *A61K 31/265* (2006.01)
  *C07C 213/00* (2006.01)
  *C07C 217/00* (2006.01)
  *C07C 211/00* (2006.01)
  *C07C 55/00* (2006.01)
  *C07C 55/06* (2006.01)

(52) U.S. Cl.
  USPC ........... 514/557; 514/512; 564/360; 564/336; 562/590; 562/597

(58) Field of Classification Search
  USPC ........... 514/557, 512; 564/360, 336; 562/590, 562/597
  See application file for complete search history.

(56) References Cited

U.S. PATENT DOCUMENTS

| | | | |
|---|---|---|---|
| 3,494,954 | A | 2/1970 | Allen et al. |
| 4,283,418 | A | 8/1981 | Fujii et al. |
| 4,535,186 | A | 8/1985 | Husbands et al. |
| 4,845,098 | A | 7/1989 | Kraemer et al. |
| 6,197,828 | B1 | 3/2001 | Jerussi et al. |
| 6,333,198 | B1 | 12/2001 | Edmeades et al. |
| 6,350,912 | B1 | 2/2002 | Chavan et al. |
| 6,673,838 | B2 | 1/2004 | Hadfield et al. |
| 6,689,912 | B2 | 2/2004 | Weber |
| 7,026,508 | B2 | 4/2006 | Winkley et al. |
| 7,026,513 | B2 | 4/2006 | Saigal et al. |
| 7,605,290 | B2 | 10/2009 | Niddam-Hildesheim et al. |
| 2002/0022662 | A1 | 2/2002 | Yardley et al. |
| 2002/0120164 | A1 | 8/2002 | Chavan et al. |
| 2003/0045583 | A1 | 3/2003 | Hadfield et al. |
| 2004/0106818 | A1 | 6/2004 | Zhiyin et al. |
| 2004/0181093 | A1 | 9/2004 | Kim et al. |
| 2005/0009870 | A1 | 1/2005 | Sher et al. |
| 2005/0096479 | A1 | 5/2005 | Hadfield et al. |
| 2005/0197392 | A1 | 9/2005 | Jerussi et al. |
| 2006/0047125 | A1 | 3/2006 | Leonardi et al. |
| 2007/0037884 | A1 | 2/2007 | Hadfield et al. |
| 2007/0135449 | A1 | 6/2007 | Mahaney et al. |
| 2008/0221356 | A1 | 9/2008 | Niddam-Hildesheim et al. |
| 2009/0069601 | A1 | 3/2009 | Niddam-Hildesheim et al. |

FOREIGN PATENT DOCUMENTS

| | | |
|---|---|---|
| CN | 1240206 | 1/2000 |
| EP | 0 112 669 A2 | 7/1984 |
| GB | 2 173 787 A | 10/1986 |
| IN | 1089/KOL/2007 | 7/2009 |
| JP | 53-31642 | 3/1978 |
| JP | 10-204057 | 8/1998 |
| JP | 2000-319288 | 11/2000 |
| WO | WO-96/20160 | 7/1996 |
| WO | WO-00/32555 | 6/2000 |
| WO | WO-00/59851 | 10/2000 |
| WO | WO-02/18325 | 3/2002 |
| WO | WO-02/50017 | 6/2002 |
| WO | WO-02/064543 | 8/2002 |
| WO | WO-03/000652 | 1/2003 |
| WO | WO-03/048104 | 6/2003 |
| WO | WO-2005/049560 | 6/2005 |
| WO | WO-2007/000294 | 1/2007 |
| WO | WO-2007/005961 | 1/2007 |
| WO | WO-2007/011594 | 1/2007 |
| WO | WO-2007/067501 | 6/2007 |
| WO | WO-2007/071404 | 6/2007 |
| WO | WO-2007/120923 | 10/2007 |
| WO | WO-2007/147564 | 12/2007 |
| WO | WO-2008/013995 | 1/2008 |
| WO | WO-2008/015584 | 2/2008 |
| WO | WO 2008/017886 | 2/2008 |
| WO | WO 2008/047167 | 4/2008 |
| WO | WO-2009/053840 | 4/2009 |
| WO | WO-2009/070311 | 6/2009 |
| WO | WO-2009/101458 | 8/2009 |
| WO | WO-2009/114685 | 9/2009 |

OTHER PUBLICATIONS

Klamerus, K. J., et al., "Introduction of the Composite Parameter to the Pharmacokinetics of Venlafaxine and its Active O-Desmethyl Metabolite", J. Clin. Pharmacol., 1992, vol. 32, pp. 716-724.

International Search Report of Application PCT/US07/009560, dated Nov. 26, 2007.

International Search Report of PCT/US2008/013170 dated Sep. 29, 2009.

(Continued)

*Primary Examiner* — Kendra D Carter  
(74) *Attorney, Agent, or Firm* — Kenyon & Kenyon LLP

(57) ABSTRACT

Provided are crystalline forms of O-desmethylvenlafaxine fumarate, methods for their preparation, and pharmaceutical composition thereof.

10 Claims, 6 Drawing Sheets

(56) References Cited

OTHER PUBLICATIONS

Caira, Mino R., "Crystalline Polymorphism of Organic Compounds", Topics in Current Chemistry, 1998, vol. 198, pp. 163-208.
Yardley, John P., et al., 2-Phenyl-2-(1-hydroxycycloalkyl)ethylamine Derivatives: Synthesis and Antidepressant Activity, J. Med. Chem. (1990) 33, pp. 2899-2905, XP000891765.
Third Party Observation at the EPO for EP Patent Application No. 07755729.6.
Database Beilstein, Beilstein Institute for Organic Chemistry, retrieved from XFIRE, XP002466133; Database accession No. BRN 4915303 abstract & Bull. Soc. Chim. Fr (1967) pp. 2110-2116.
Database Beilstein, Beilstein Institute for Organic Chemistry, retrieved from XFIRE, XP002466134; Database accession No. BRN 509825 abstract & Justus Liebigs Ann. Chem., vol. 322 (1902) p. 160.
Database Beilstein, Beilstein Institute for Organic Chemistry, retrieved from XFIRE, XP002466135; Database accession No. BRN 8340448 abstract & J. Org. Chem., vol. 64, No. 13 (1999) pp. 4887-4892.
Database Beilstein, Beilstein Institute for Organic Chemistry, retrieved from XFIRE, XP002466136; Database accession No. BRN 8551248 abstract & J. Med. Chem., vol. 42, No. 22 (1999) pp. 4680-4694.
Database Beilstein, Beilstein Institute for Organic Chemistry, retrieved from XFIRE, XP002466137; Database accession No. BRN 3314063 abstract & Org. Lett., vol. 8, No. 5 (2006) pp. 1007-1009.
Database Beilstein, Beilstein Institute for Organic Chemistry, retrieved from XFIRE, XP002466138; Database accession No. BRN 3252517 abstract & Yakugaku Zasshi, vol. 59 (1939) pp. 547-549.
Miyakawa, M. & Scanlan, T.S., "Synthesis of [$^{125}$I]-, [$^{2}$H]-, and [$^{3}$H]-Labeled 3-Iodothyronamine (T$_1$AM)," Synthetic Communications, vol. 36 (Mar. 1, 2006) pp. 891-902, XP002466132.
Strobel, H.A. et al., "Chemical Instrumentation: A Systematic Approach," 3$^{rd}$ ed., Wiley & Sons, New York 1989, p. 922-953.
Strobel, H.A. et al., "Chemical Instrumentation: A Systematic Approach," 3$^{rd}$ ed., Wiley & Sons, New York 1989, pp. 391-393, 921-922, 924-925.
Carey et al., Advanced Organic Chemistry: Reactions and Synthesis: Part B, 4$^{th}$ ed., p. 822 (2000).
Cheng, Guohou et al., "Process for preparing 1-[2-(2-(dimethylamino)-1-(4-methoxyphenyl)ethyl]cyclohexanol hydrochloride," Database CA [Online] Chemical Abstracts Service, Columbus, Ohio, US; XP002466013 retrieved from STN Database accession No. 133:252074 abstract & CN 1 240 206 A (Huadong Science and Engineering Univ., Peop. Rep. China, Jan. 5, 2000).
Database Beilstein, Beilstein Institute for Organic Chemistry, Frankfurt-Main, DE; XP002466014, retrieved from XFIRE Database accession No. BRN 7872599 abstract & J. Labelled Compd Radiopharm, vol. 40, pp. 762-763 (1997).
Database Beilstein, Beilstein Institute for Organic Chemistry, Frankfurt-Main, DE; XP002466015, retrieved from XFIRE Database accession No. BRN 4194092 abstract & J. Med. Chem., vol. 33, No. 10, pp. 3899-2905 (1990).
Stefanovskii, Yu. N. et al., "Synthesis, configuration and reduction of dimethyiamides of some (+−)-threo-3-hydroxy-2, 3-diarylpropanoic acids to aminopropanols," Database CA [Online] Chemical Abstracts Service, Columbus, Ohio, US; XP002466016 retrieved from STN Database accession No. 69:26952 abstract & Comptes Rendus De L'Academie Bulgare Des Sciences, 21(3), 249-252, CODEN:CRABAA (1968).
Fanali et al., "Use of vancomycin silica stationary phase in packed capillary electrochromatography II. Enantiomer separation of venlafaxine and O-desmethylvenlafaxine in human plasma," J. of Chromatography, 919: 195-203 (2001).
Freudenreich, Charles et al., "Design of inhibitors from the three-dimensional structure of alcohol dehydrogenase. Chemical synthesis and enzymic properties," Database CA [Online] Chemical Abstracts Service, Columbus, Ohio, US; XP002466017, retrieved from STN Database accession No. 100:205537 abstract & J. American Chem. Soc., No. 106, vol. 11, pp. 3344-3353 CODEN: JACSAT; ISSN:0002-7863 (1984).
E.J. Baran: "The saccarinate anion: a versatile and fascinating ligand in coordination chemistry", Quimica Nova, vol. 28, No. 2, 2005, pp. 326-328, XP002503521, BR Sociedade Brasileira de Quimica, Sao Paulo.
Chavan, S.P., et al., "An efficient and green protocol for the preparation of cycloalkanols: a practical synthesis of venlafaxine," Tetrahedron Letters (2004) vol. 45, pp. 7291-7295, XP002419152.
Greene, "Protection for 2-Hydroxybenzenethiols", Protective Groups in Organic Synthesis, p. 248 (1999).
Greene, "Protection for the Amino Group", Protective Groups in Organic Synthesis, p. 494-653 (1999).
Hashemi et al, "A Novel and Simple Solvent Free Method for Nucleophilic Aromatic substitution of Inactive Aryl Halides" Synthetic Communications, vol. 34, No. 45, pp. 2783-2787 (2004).
Hawthorne, "Simple Procedure for the Conversion of Aryl Halides to the Corresponding Phenols", J. Org. Chem., p. 1001 (1957).
Perry's Chemical Engineer's Handbook, pp. 20-54 to 20-57 (Sixth Edition 1984).
ICH Good Manufacturing Practice Guide for Active Pharmaceutical Ingredients, Q7A, Current Step 4 Version (Nov. 10, 2000).
Snyder, L.R., et al., Introduction to Modern Liquid Chromatography, 549, 552, 571-572, 2d ed. (John Wiley & Sons, New York 1979).
G.P.R. Carr, "The Development of British Pharmacopoeia Monographs for Idoxuridine and Idoxuridine Eye Drops Using High-Pressure Liquid Chromatography for Essay and for Controlling Related Impurities", Journal of Chromatography, 157 (1978), pp. 171-184.
Hicks, David. R. et al., "A High-Performance Liquid Chromatographic Methods for the Simultaneous Determination of Venlafaxine and O-Desmethylvenlafaxine in Biological Fluids", Therapeutic Drug Monitoring, vol. 16, (1994), pp. 100-107.
Kumar, Phani. A. et al., "A Validated Reversed Phase HPLC Method for the Determination of Process-Related Impurities in Almotriptan Malate API", Journal of Pharmaceutical and Biomedical Analysis, vol. 46, No. 4, (2007), pp. 792-798.
Rao, Nageswara. R. et al., "An Overview of the Recent Trends in Development of HPLC Methods for Determination of Impurities in Drugs", Journal of Pharmaceutical and Biomedical Analysis, vol. 33, No. 3, (2003), pp. 335-377.
Nayak, et al., Chemoselective aryl alkyl ether cleavage by thiophenolate anion through its in situ generation in catalytic amount, Tetrahedron Letters, vol. 38, No. 50, pp. 8479-8751 (1997).
Japanese Office Action of JP2007-194774 mailed on Jun. 8, 2010.
Japanese Office Action of JP2007-194720, mailed on Jun. 8, 2010.
Shen, et al., Database CA, Chemical Abstract Service Columbus, Ohio, retrieved from STN, XP002557225, Database accession No. 2007:1399708, CN 101 081 815; Beijing Hope International Pharmaceutical Co., Ltd (2007).
Shen, et al., Database CA, Chemical Abstract Service Columbus, Ohio, retrieved from STN, XP002557224, Database accession No. 2007:1399710, CN 101 081 816; Beijing Hope International Pharmaceutical Co., Ltd (2007).

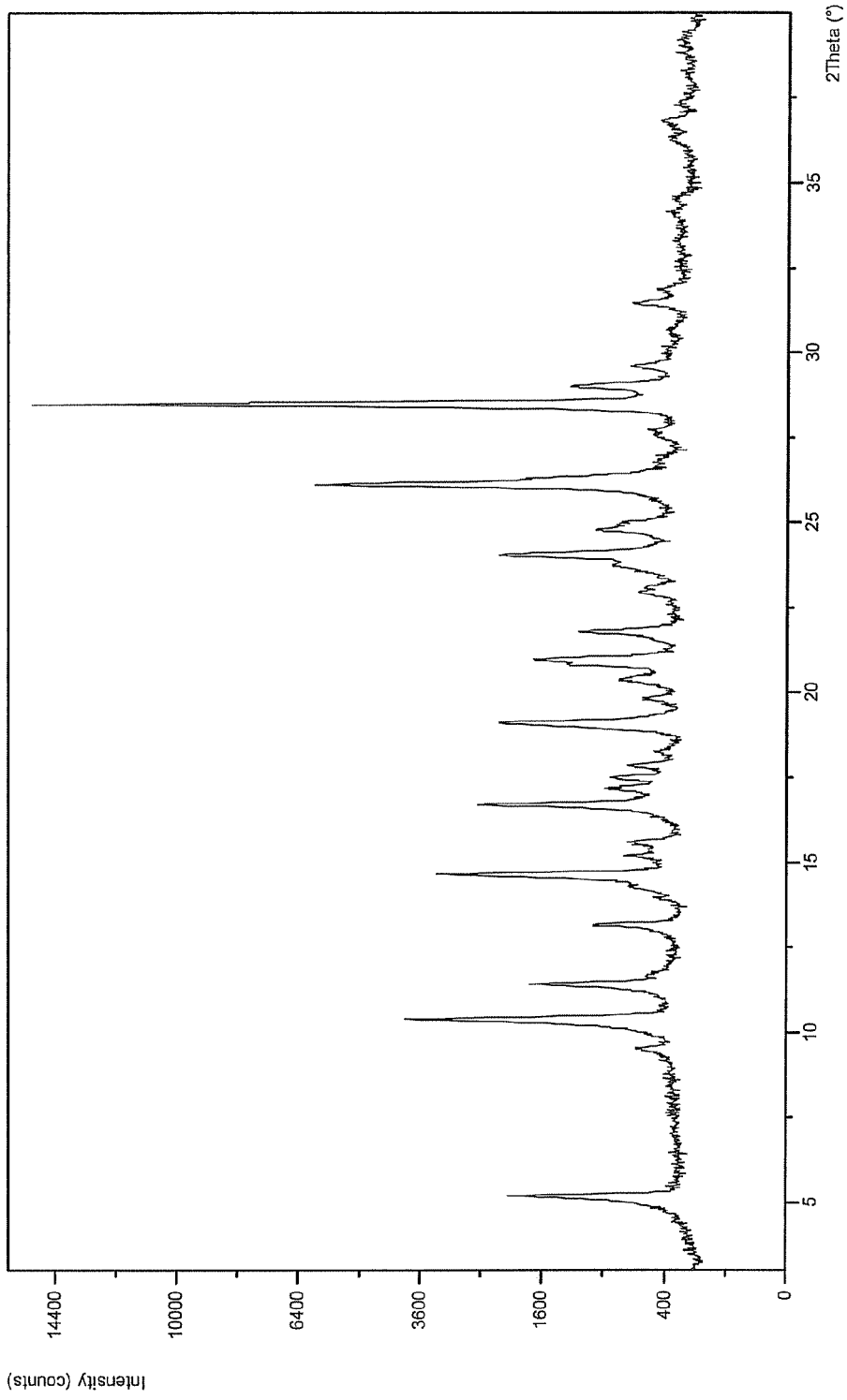
Figure 1 shows a powder XRD pattern of O-desmethylvenlafaxine fumarate, Form N_(peak at 28.46 ± 0.2 degrees 2-theta belongs to Silica powder).

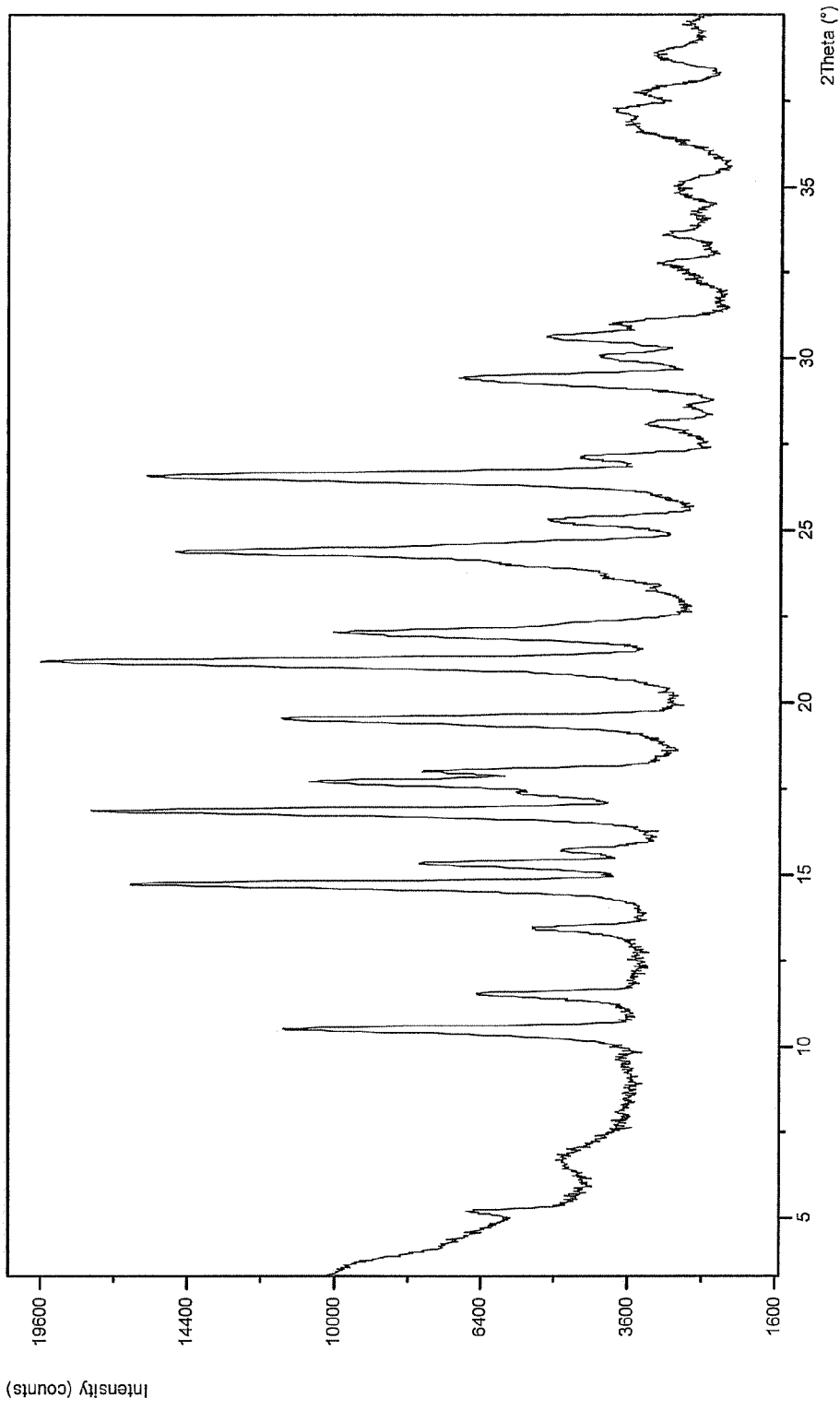
Figure 2. shows a powder XRD pattern of O-desmethylvenlafaxine fumarate, Form D.

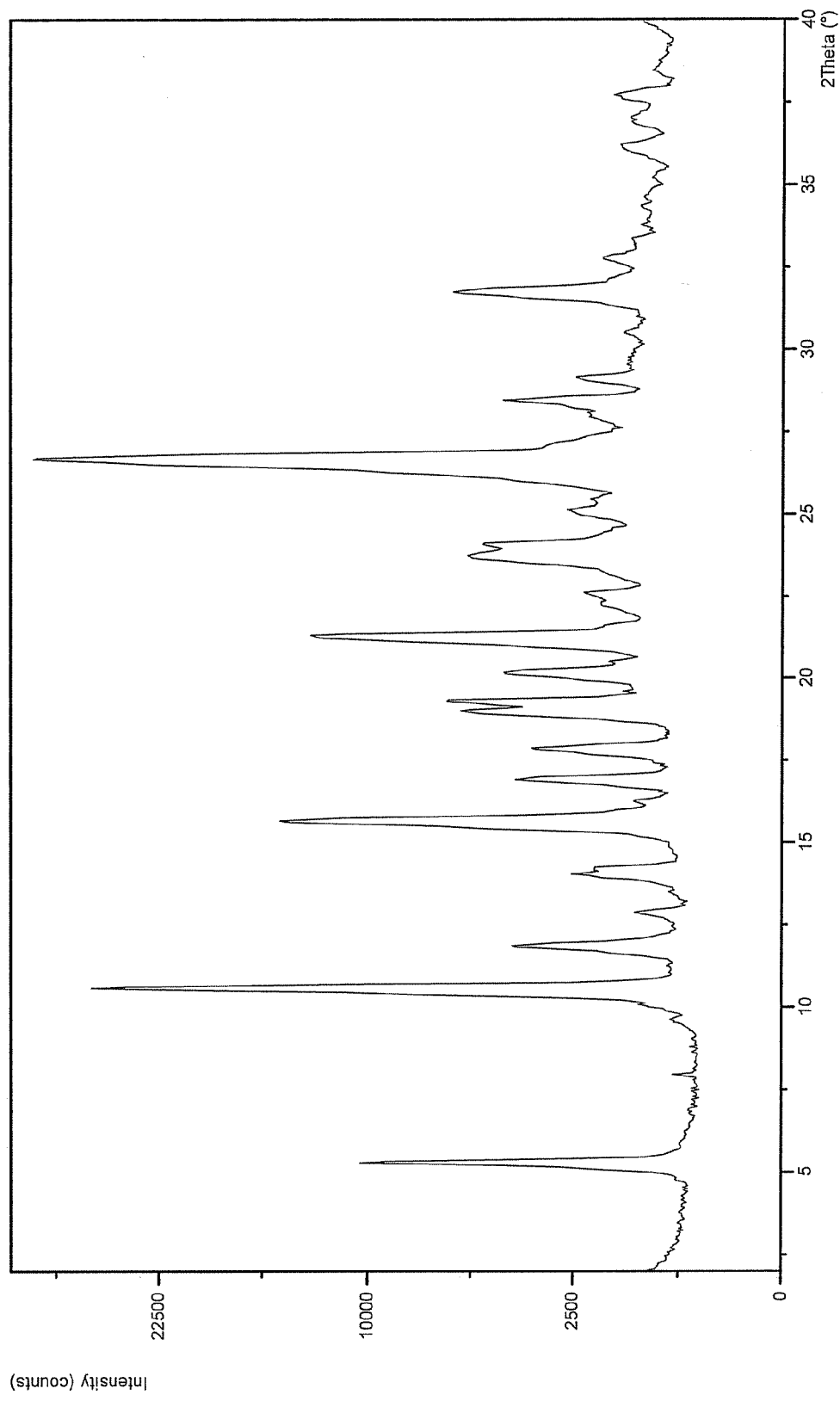
Figure 3. shows a powder XRD pattern of O-desmethylvenlafaxine fumarate, Form X

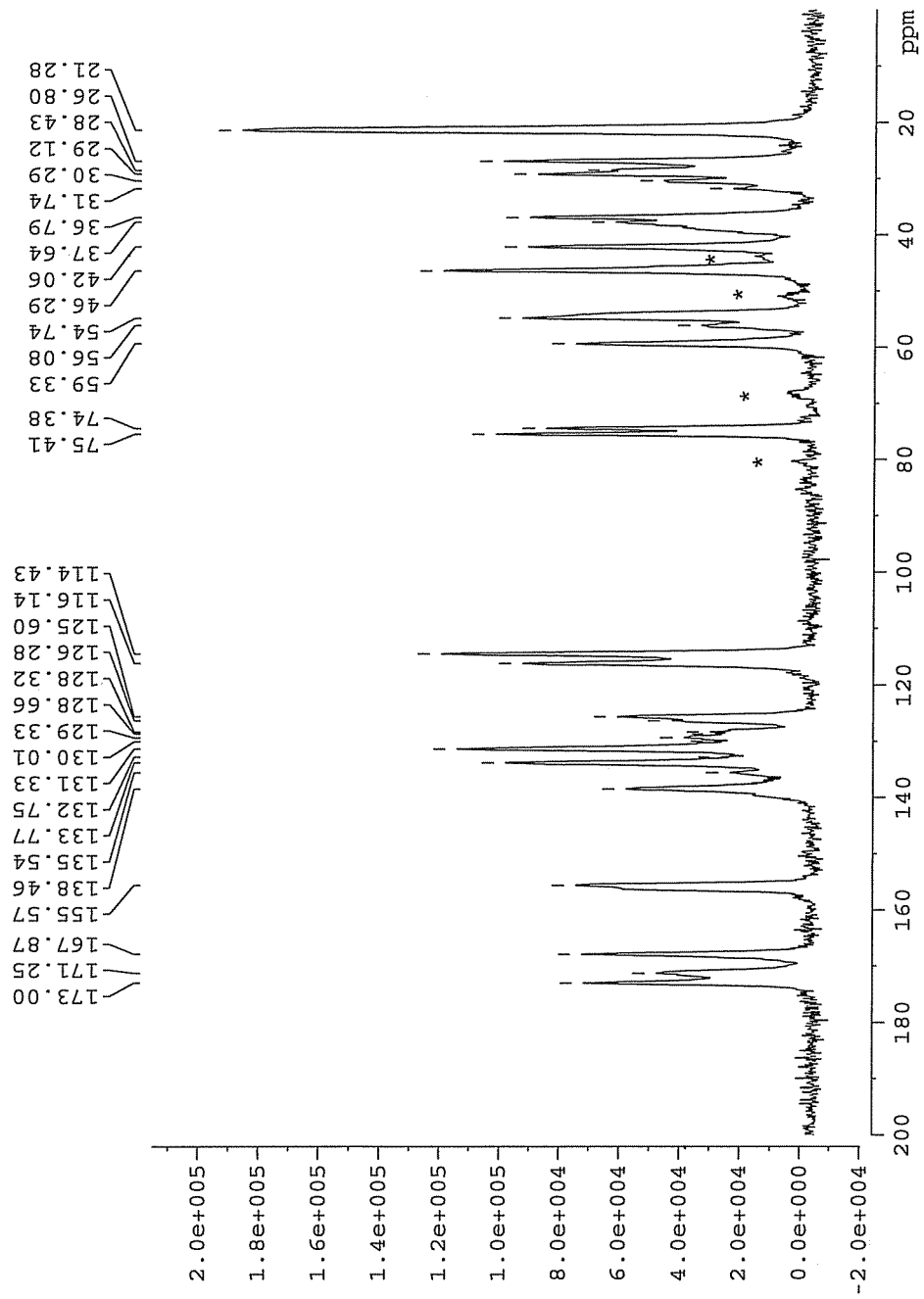
Figure 4 shows a solid state $^{13}$C NMR spectrum of O-desmethylvenlafaxine fumarate, form N

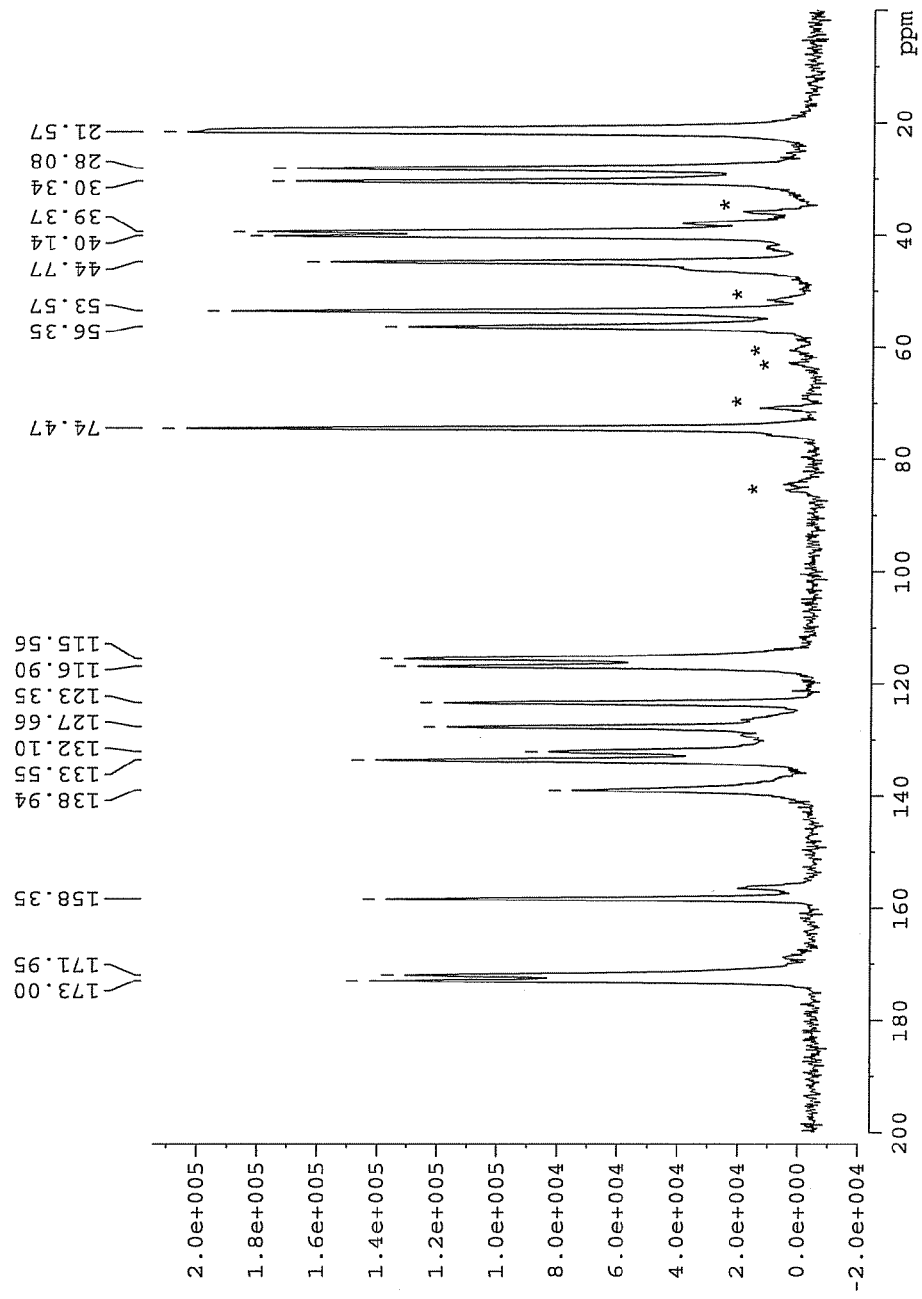
Figure 5 shows a solid state $^{13}$C NMR spectrum of O-desmethylvenlafaxine fumarate, form X in mixture with small amount of Form I.

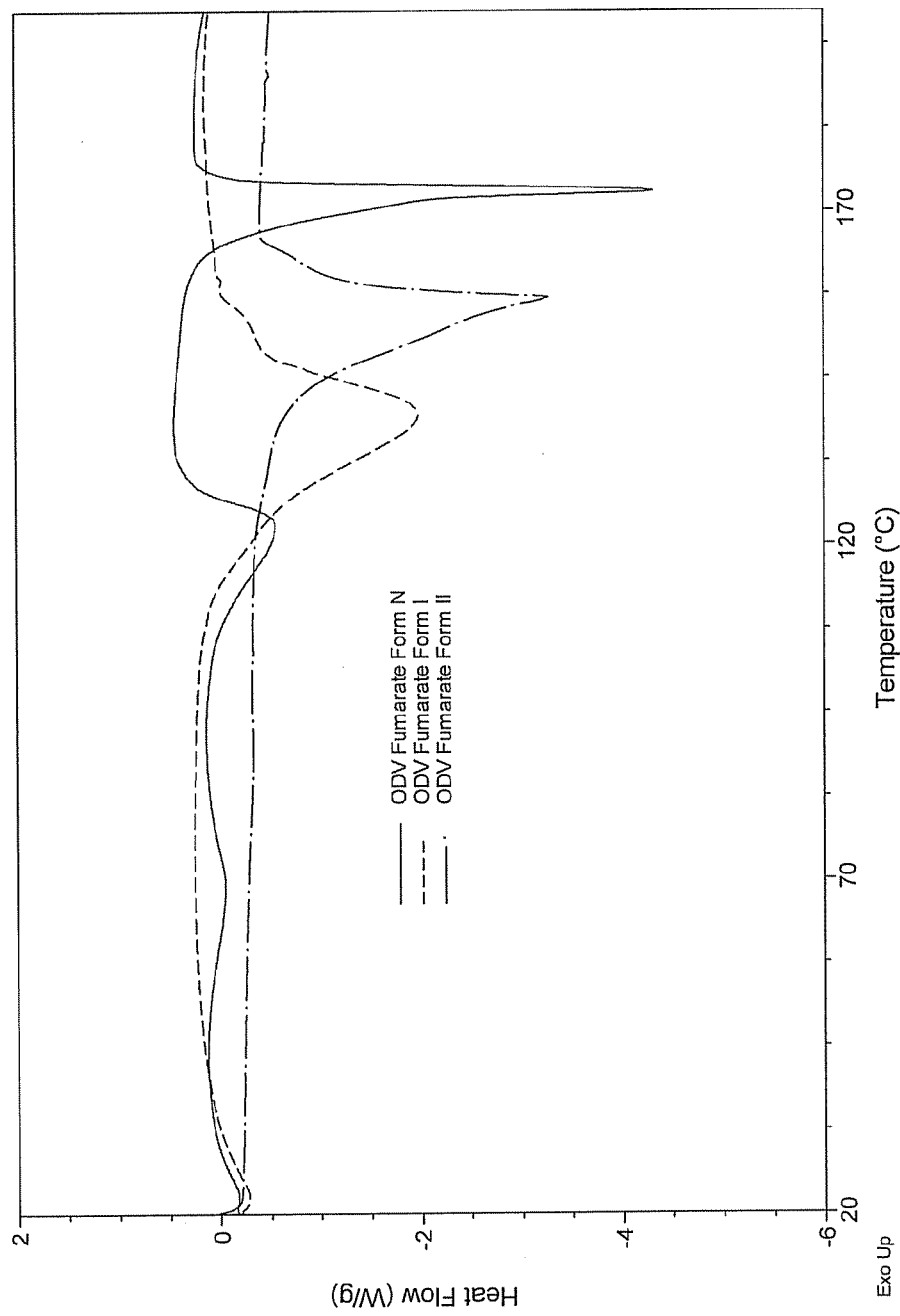
Figure 6 shows a compared DSC curves of O-desvenlafaxine fumarate Form I, Form II and Form N

CRYSTAL FORMS OF O-DESMETHYLVENLAFAXINE FUMARATE

CROSS REFERENCE TO RELATED APPLICATIONS

The present application claims the benefits of the following U.S. Provisional Patent Application Nos. 61/318,638 filed Mar. 29, 2010; and 61/327,239 filed Apr. 23, 2010. The contents of these applications are incorporated herein by reference.

FIELD OF INVENTION

The present invention is directed to crystalline forms of O-desmethylvenlafaxine fumarate and methods of preparation thereof.

BACKGROUND OF THE INVENTION

Venlafaxine, (±)-1-[2-(dimethylamino)-1-(4-ethyoxyphenyl)ethyl]cyclo-hexanol, having the following formula I, is the first of a class of anti-depressants. Venlafaxine acts by inhibiting re-uptake of norepinephrine and serotonin, and is an alternative to the tricyclic anti-depressants and selective re-uptake inhibitors.

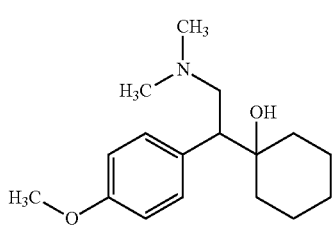

Formula I

O-Desmethylvenlafaxine, chemically named 4-[2-(dimethylamino)-1-(1-hydroxycyclohexyl)ethyl]phenol and having the following formula II

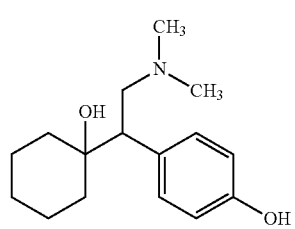

Formula II $C_{16}H_{25}NO_2$
Mol. Wt: 263.38 is a major metabolite of venlafaxine and has been shown to inhibit norepinephrine and serotonin uptake. Klamerus, K. J. et al., "Introduction of the Composite Parameter to the Pharmacokinetics of Venlafaxine and its Active O-Desmethyl Metabolite", *J. Clin. Pharmacol.* 32:716-724 (1992).

O-Desmethylvenlafaxine and processes for preparation thereof are described in U.S. Pat. Nos. 6,197,828 and 6,689,912, and in US 2005/0197392, all of which are incorporated herein by reference.

The fumarate salt of O-desmethylvenlafaxine, is chemically named -[2-(dimethyl-amino)-1-(4-phenol)ethyl]-cyclohexanol fumarate, and has the following formula III

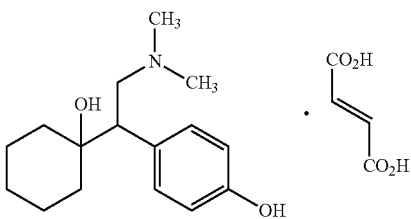

Formula III

Several pharmaceutically acceptable salts of O-desmethylvenlafaxine are described in U.S. Pat. No. 4,535,186. In Example 26 of this reference, a preparation of the fumarate salt is described. The product is reported to have a melting point range of 140° C.-142° C. WO2009070311 describes two pure polymorphic forms of O-desmethylvenlafaxine fumarate, Forms I and II. WO2009101458 discloses an amorphous form of O-desmethylvenlafaxine fumarate, and four polymorphic forms: Forms I, II, amorphous, III and Form IV.

Polymorphism, the occurrence of different crystal forms, is a property of some molecules and molecular complexes. A single molecule, like O-desmethylvenlafaxine, may give rise to a variety of polymorphs having distinct crystal structures and physical properties like melting point, thermal behaviours (e.g. measured by thermogravimetric analysis—"TGA", or differential scanning calorimetry—"DSC"), X-ray diffraction (XRD) pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of O-desmethylvenlafaxine and O-desmethylvenlafaxine salts.

The present invention comprises new solid state forms of O-desmethylvenlafaxine fumarate salt.

SUMMARY OF THE INVENTION

The present invention provides new solid state forms of O-desmethylvenlafaxine fumarate, processes for preparing them, and pharmaceutical composition containing them.

In one embodiment, the present invention comprises the use of one or more of the above described polymorphic forms of O-desmethylvenlafaxine fumarate for the preparation of O-desmethylvenlafaxine succinate or formulation thereof.

In another embodiment, the present invention comprises a pharmaceutical composition comprising one or more of the polymorphic forms of O-desmethylvenlafaxine fumarate described herein, and at least one pharmaceutically acceptable excipient.

BRIEF DESCRIPTION OF THE FIGURES

FIG. 1 shows a powder XRD pattern of O-desmethylvenlafaxine fumarate form N, wherein the peak at 28.46±0.2 degrees 2-theta corresponds to the internal standard, Silica powder.

FIG. 2 shows a powder XRD pattern of O-desmethylvenlafaxine fumarate form D, wherein the peak at 28.46±0.2 degrees 2-theta corresponds to the internal standard, Silica powder.

FIG. 3 shows a powder XRD pattern of O-desmethylvenlafaxine fumarate form X, wherein the peak at 28.46±0.2 degrees 2-theta corresponds to the internal standard, silica powder.

FIG. 4 shows a solid state $^{13}$C NMR spectrum of O-desmethylvenlafaxine fumarate form N FIG. 5 shows a solid state $^{13}$C NMR spectrum of O-desmethylvenlafaxine fumarate form X in mixture with small amount of form I.

FIG. 6 shows a comparison of DSC curves of O-desmethylvenlafaxine fumarate Form I, Form II and Form N

DETAILED DESCRIPTION OF THE INVENTION

The present invention relates to polymorphs of O-desmethylvenlafaxine fumarate, processes for preparing said polymorphs, and pharmaceutical compositions comprising said polymorphs.

A crystal form may be referred to herein as being characterized by graphical data "as shown in," or "as depicted in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form, and confirm whether the two sets of data are characterizing the same crystal form or two different crystal forms.

A polymorphic form according to the invention may be referred to herein as "pure" or "polymorphically pure." This terminology refers to the subject polymorph containing less than about 20% (w/w) of other polymorphic forms. Preferably, when a crystal form according to the invention is referred to as pure of polymorphically pure, it will contain less than 10%, less than 5%, less than 2%, less than 1% or even less than 0.5% of other forms of the compound. In other embodiments, the polymorphs of O-desmethylvenlafaxine fumarate according to the invention may contain from 1% to 20% (w/w), from 5% to 20% (w/w), or from 5% to 10% (w/w) of one or more other polymorphic forms of O-desmethylvenlafaxine fumarate.

As used herein, the term chemical shift difference refers to the difference in chemical shifts between a reference signal and another signal in the same NMR spectrum. These chemical shift differences serve to provide an additional analytical measurement for a substance, for example a O-desmethylvenlafaxine salt of the present invention, which will compensate for a phenomenon that may occur in NMR spectroscopy wherein a shift in the solid-state NMR "fingerprint" is observed. Such a shift in the NMR peaks may occur, for example as a result of variations in the instrumentation, the temperature, or the calibration method used in the NMR analysis. This shift in the solid-state NMR "fingerprint", having chemical shift resonances at a certain positions, is such that even though the individual chemical shifts of signals have moved, all the peaks in the spectrum are moved be the same amount, such that the difference between chemical shifts of each signal and another is retained and may be used as a reliable characterization of the material being analyzed.

In the present patent application the chemical shift differences were calculated by subtracting the chemical shift value of the signal exhibiting the lowest chemical shift (reference signal) in the solid state $^{13}$C NMR spectrum in the range of 100 to 180 ppm from chemical shift value of another (observed) signal in the same $^{13}$C NMR spectrum in the range of 100 to 180 ppm.

As used herein, the term "monohydrate" refers to hydrate containing water in crystal lattice, in equimolar amount compared to the compound. In particularly, the compound is O-desmethylvenlafaxine fumarate.

As used herein, the expression "room temperature" refers to a temperature between about 20° C. and about 30° C. Usually, room temperature ranges from about 20° C. to about 25° C.

As used herein, the term "dry crystalline form" refers to a polymorph that was dried using any conventional techniques to remove residual solvent. Examples for such conventional techniques can be, but not limited to, evaporation, vacuum drying, oven drying, drying under nitrogen flow etc.

As used herein, the teen "Overnight" refers to a period of between about 15 and about 20 hours, typically between about 16 to about 20 hours.

In one embodiment the present invention comprises a crystalline form of O-desmethylvenlafaxine fumarate designated form N. Form N can be characterized by data selected from: a powder XRD pattern with peaks at about 9.5, 13.2, 14.6, 21.8 and 24.8° 2θ±0.2° 2θ; a powder XRD pattern as depicted in FIG. 1, a $^{13}$C NMR spectrum having signals at about 167.87, 131.33 and 114.43±0.2 ppm; a solid state $^{13}$C NMR spectrum as depicted in FIG. 4, and combinations thereof. O-Desmethylvenlafaxine fumarate crystalline Form N can be further characterized by additional PXRD peaks at about 5.2, 10.4, 16.7 and 26.1° 2θ±0.2° 2θ. Form N of O-desmethylvenlafaxine fumarate can be a monohydrate.

In a preferred embodiment, form N can be polymorphically pure.

In certain embodiments, the invention encompasses polymorphically pure form N containing not more than about 10% by weight, preferably, not more than 5%, and more preferably, not more than 1% by weight, of O-Desvenlafaxine fumarate Form D.

The amount of O-Desvenlafaxine fumarate form D in O-Desvenlafaxine fumarate form N can be determined by PXRD using any one of the peaks at 13.5 and 19.6 degree two-theta.

Crystalline O-desmethylvenlafaxine fumarate form N has advantageous properties selected from at least one of: chemical purity, flowability, solubility, morphology or crystal habit, stability—such as storage stability, stability to dehydration, stability to polymorphic conversion, low hygroscopicity, low content of residual solvents. Particularly, the crystalline O-desmethylvenlafaxine fumarate form N of the present invention has advantageous stability.

O-Desvenlafaxine fumarate Form N exhibits enhanced thermal stability as compared to forms I and II. As can be seen from the comparison of DSC (Differential Scanning Calorimetry) curves of the three forms (FIG. 6), the melting process of O-Desvenlafaxine fumarate form N occurs at a temperature 34° C. higher than that of Form I and at 16° C. higher than that of Form II.

In another embodiment, the present invention comprises a crystalline form of O-desmethylvenlafaxine fumarate designated form X. Form X can be characterized by data selected from: a powder XRD pattern with peaks at about 11.9, 14.0, 15.7, 21.3 and 26.7±0.2° 2θ; a powder XRD pattern as depicted in FIG. 3, a $^{13}$C NMR spectrum having signals at about 158.35, 123.35 and 74.47±0.2 ppm; a solid state $^{13}$C NMR spectrum as depicted in FIG. 5, and combinations thereof. O-Desmethylvenlafaxine fumarate crystalline Form X can be further characterized by a powder XRD pattern having additional peaks at about 5.3, 10.6, 12.9, 19.3 and 29.1° 2θ±0.2° 2θ.

The present invention also comprises a crystalline form of O-desmethylvenlafaxine fumarate designated form D. Form D can be characterized by data selected from: a powder XRD pattern with peaks at about 10.6, 13.5, 14.8, 24.5 and 26.7° 2θ±0.2° 2θ; a powder XRD pattern as depicted in FIG. 2, and combinations thereof. O-Desmethylvenlafaxine fumarate crystalline Form D can be further characterized by additional powder XRD peaks at about 5.3, 10.6, 19.6, 21.3 and 29.6° 2θ±0.2° 2θ.

The present invention further encompasses 1) a pharmaceutical composition comprising the above described crystalline forms and at least one pharmaceutically acceptable excipient; 2) the use of any one or combination of the above described crystalline forms and another carboxylic acid in the manufacture of a pharmaceutical composition, and 3) a method of treating depression, comprising administering a pharmaceutically effective amount of at least one of the above described crystalline forms to a subject in need of the treatment. The pharmaceutical composition can be useful for preparing a medicament. The present invention also provides at least one of the above described crystalline forms for use as a medicament.

The above described polymorphs of O-desmethylvenlafaxine fumarate can be used to prepare O-desmethylvenlafaxine succinate or formulations thereof by any method known in the art.

In a preferred embodiment, O-desmethylvenlafaxine succinate is prepared by reacting O-desmethylvenlafaxine fumarate with a base to obtain O-desmethylvenlafaxine base and further reacting with succinic acid to obtain O-desmethylvenlafaxine succinate.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

PXRD Method A

After being powdered using a mortar and pestle, samples were applied directly on a silicon plate holder. The X-ray powder diffraction pattern was measured with a Philips X'Pert PRO X-ray powder diffractometer, equipped with a Cu irradiation source=1.54184 Å (Angström), X'Celerator (2.022° 2Θ) detector. Scanning parameters: angle range: 3-40 deg., step size 0.0167, time per step 37 s, continuous scan. The described peak positions were determined using silicon powder as an internal standard in an admixture with the sample measured. The position of the silicon (Si) peak was corrected to silicone theoretical peak: 28.45 degrees two theta, and the positions of the measured peaks were corrected respectively. No correction was performed on the diffractograms depicted in FIGS. 1 and 2.

PXRD Method B

Samples after being powdered using mortar and pestle, are applied directly on standard PMMA sample holder with silicon low background Ø 51.5 mm with Ø 20 mm×0.5 mm sample cavity. The X-ray powder diffraction pattern was measured with Bruker Advance D8 X-ray powder diffractometer, equipped with Cu irradiation source=1.54184 Å (Angström), Lynx Eye detector. Scanning parameters: angle range: 2-40 deg., step size 0.5, time per step 0.5 s, continuous scan. The described peak positions were determined using silicon powder as an internal standard in an admixture with the sample measured. The position of the silicon (Si) peak was corrected to silicone theoretical peak: 28.45 degrees two theta, and the positions of the measured peaks were corrected respectively. No correction was performed on the presented diffractogram in FIG. 3.

$^{13}$C NMR Method

Solid-state $^{13}$C NMR spectra were recorded with variable amplitude cross polarization, magic angle spinning and high power proton decoupling using a BRUKER Avarice II+ spectrometer operating at 125 MHz and ambient temperature (about 25° C.—not controlled). A probe using 4 mm o.d. zirconia rotors was employed. The operation conditions were: contact time: 2 ms; recycle delay: 2 s 1024 scans; spin rate of 11 kHz. Chemical shifts were referenced via a replacement sample of glycine (carboxyl carbon chemical shift assigned as 176.03 ppm relative to the signal of tetramethylsilane).

Differential Scanning Calorimetry (DSC)

A. Equipment
Instrument: TA Universal Analysis Q1000
Software: Universal Analysis 2000
B. Experimental Parameters
Heating rate: 10° C./min
Temperature range: 20-200° C.
Sample size: 2.00-5.00 mg
Purge gas: Nitrogen, 40 ml/min
Crucible: Hermetic pinholed

EXAMPLES

Example 1

Preparation of O-Desmethylvenlafaxine Fumarate, Form N

To a 1000 ml flask equipped with a mechanical stirrer and condenser, O-Desmethyl venlafaxine base (50 g), fumaric acid (24.24 g), and isopropyl alcohol (IPA) (1000 ml) were added at room temperature to form a mixture. The mixture was then heated to reflux. A clear solution was obtained after filtering the heated mixture through a 1-micron filter. The filtered solution was cooled to 50° C., and then gradually cooled to 5° C. over five hrs. The cooled solution was stirred at 5° C. overnight. The mixture was then heated back to 50° C., stirred at 50° C. for 2 hrs, and then cooled back to 5° C. and stirred at 5° C. for 3 hrs. A solid precipitate formed and was filtered under reduced pressure, washed with IPA, and dried in a vacuum oven, overnight, at 50° C. The obtained solid was kept in a closed container at 4° C. for five weeks, after which Form N was obtained.

Example 2

Preparation of O-Desmethylvenlafaxine Fumarate, Form D

About 50 mg of a sample of form N was put in a sample holder for Anton Paar temperature controlled unit mounted on Philp's Xpert Pro diffractometer. The sample was heated up to 140° C. at a heating rate of 10° C./min. The observed diffraction pattern changed from Form N to Form D. The sample was cooled down to 30° C., at a cooling rate of 10° C./min. The pattern remained that of Form D. A powder XRD of the obtained Form D is shown in FIG. 2.

Example 3

Preparation of O-Desmethylvenlafaxine Fumarate, Form X

O-Desmethylvenlafaxine base (20 g) and 600 ml IPA were added to a jacketed 1 L reactor equipped with a mechanical stirrer. A nitrogen atmosphere was applied. The resulting mixture was heated to Tj (jacket temperature)=90° C. and stirred at this temperature for 30 min to ensure dissolution. The temperature was lowered to 75° C. and a mechanical filtration was performed. The resulting clear solution was cooled by applying Tj=60° C. and 179.8 g of fumaric acid was added. Precipitation started immediately after the fumaric acid addition. The mixture was stirred at Tj=60° C. for two hours, and then gradually cooled to 5° C. during two hours, and stirred at 5° C. overnight. The precipitated O-Desmethylvenlafaxine fumarate was separated by filtration and washed twice with 20 ml IPA. Wet O-Desmethylvenlafaxine Fumarate (41 g) was obtained. A portion (12.5 g) of the wet material was dried in a tray vacuum oven at 90° C. over a weekend, yielding 8 g of dry O-Desmethylvenlafaxine Fumarate Form X.

Example 4

Preparation of Crude O-Desmethylvenlafaxine Base

Didesmethylvenlafaxine ("DDMV"), HCl (100 gr), $Na_2S$ (54.6 gr) and N-methyl-2-pyrrolidone ("NMP") (200 ml) are charged into a stirred reactor. The mixture is gradually heated to 185° C. and stirred for >6 hr until reaction is completed.

The mixture is then cooled to 80-90° C. and IPA (100 ml) is added. Paraformaldehyde (31.5 gr), Formic acid (120.7 ml) and IPA (100 ml) are charged into a stirred reactor and the mixture is heated to 80-90° C. The tridesmethyl venlafaxine ("TDMV") mixture obtained in the previous reaction is then added to the reactor. The reactor is heated to 100-120° C. and the mixture is stirred for 4-8 hrs until reaction is completed. The mixture is then cooled to 20-30° C. and water (500 ml) is added. Mechanical filtration is performed (optional). NaOH 47% is added until pH=9.5-10 is obtained. The mixture is cooled to 0-10° C., stirred for >1 hr and filtered. The wet cake is washed three times with water (3×100 ml) and IPA (2×100 ml). The wet material is optionally dried under vacuum.

Example 5

Preparation of Pure O-Desmethylvenlafaxine Base

O-Desmethylvenlafaxine base crude (100 gr) and IPA (600 ml) are charged into a stirred reactor. The mixture is heated to reflux (~79-82° C.) and stirred for at least 1 hr. The mixture is then gradually cooled to 10-20° C. during 4-6 hrs and mixed at this temperature for additional 6-18 hrs. The material is filtered and the wet cake is washed with IPA (2×100 ml). The wet product is dried in a heated vacuum drier.

What is claimed is:

1. The crystalline Form N of O-desmethylvenlafaxine fumarate, characterized by data selected from: a powder XRD pattern with peaks at about 9.5, 13.2, 14.6, 21.8 and 24.8° 2θ±0.2° 2θ; a powder XRD pattern as depicted in FIG. 1, a $^{13}$C NMR spectrum having signals at about 167.87, 131.33 and 114.43±0.2 ppm; a solid state $^{13}$C NMR spectrum as depicted in FIG. 4, or combinations thereof.

2. The crystalline Form N of O-desmethylvenlafaxine fumarate according to claim 1, characterized by a powder XRD pattern with peaks at about 9.5, 13.2, 14.6, 21.8 and 24.8° 2θ±0.2° 2θ.

3. The crystalline form N of claim 2, further characterized by additional X-ray powder diffraction peaks at 5.2, 10.4, 16.7 and 26.1° 2θ±0.2° 2θ.

4. The crystalline Form N of O-desmethylvenlafaxine fumarate according to claim 1, characterized by a powder XRD pattern as depicted in FIG. 1.

5. The crystalline Form N of O-desmethylvenlafaxine fumarate according to claim 1, characterized by a $^{13}$C NMR spectrum having signals at about 167.87, 131.33 and 114.43±0.2 ppm.

6. The crystalline Form N of O-desmethylvenlafaxine fumarate according to claim 1, characterized by a solid state $^{13}$C NMR spectrum as depicted in FIG. 4.

7. The crystalline Form N of O-desmethylvenlafaxine fumarate according to claim 1, wherein the crystalline form is a monohydrate.

8. A composition containing the crystalline form of O-desmethylvenlafaxine fumarate of claim 1 and not more than about 10% by weight of a crystalline form of O-desmethylvenlafaxine fumarate characterized by a PXRD pattern having peaks at about 10.6, 13.5, 14.8, 24.5 and 26.7° 2θ±0.2° 2θ.

9. A pharmaceutical composition comprising the crystalline Form N of O-desmethylvenlafaxine fumarate according to claim 2, and at least on pharmaceutically acceptable excipient.

10. A method for treating depression, comprising administering a pharmaceutically effective amount of the crystalline Form N of O-desmethylvenlafaxine fumarate according to claim 2, to a subject in need of such treatment.

* * * * *